United States Patent [19]

MacLaury

[11] 4,192,956

[45] Mar. 11, 1980

[54] DEHYDROHALOGENATION OF A DIPHENYL TRICHLOROETHANE

[75] Inventor: Michael R. MacLaury, Rexford, N.Y.

[73] Assignee: General Electric Company, Schenectady, N.Y.

[21] Appl. No.: 11,103

[22] Filed: Feb. 12, 1979

[51] Int. Cl.$^2$ ............................................ C07C 37/00
[52] U.S. Cl. .................................................. 568/726
[58] Field of Search ........................................ 568/726

[56] References Cited

U.S. PATENT DOCUMENTS

| 4,097,538 | 6/1978 | Factor et al. | 568/726 |
| 4,117,018 | 9/1978 | Cleveland et al. | 568/726 |

*Primary Examiner*—Norman Morgenstern
*Attorney, Agent, or Firm*—Joseph T. Cohen; Leo I. MaLossi

[57] ABSTRACT

The action of liquid ammonia in dehydrohalogenating 1,1,1-trichloro-2,2-bis(4-hydroxyphenyl)ethane to 1,1-dichloro-2,2-bis(4-hydroxyphenyl)ethylene by liquid ammonia can be accelerated by incorporating in the liquid ammonia an effective amount of a certain class of inorganic salts.

8 Claims, No Drawings

DEHYDROHALOGENATION OF A DIPHENYL TRICHLOROETHANE

This invention is concerned with a process for dehydrohalogenating a dihydroxy diphenyl trichloroethane. More particularly, the invention is concerned with a process for obtaining in good yield, high purity and at an increased rate of reaction the compound 1,1-dichloro-2,2-bis(4-hydroxyphenyl)ethylene (hereinafter referred to as "dichloride") having the formula

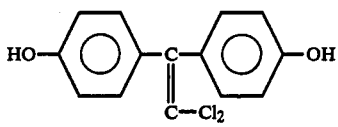

by treating 1,1,1-trichloro-2,2-bis(4-hydroxyphenyl)ethane (hereinafter referred to as "trichloride") having the formula

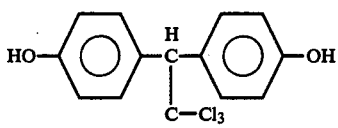

with anhydrous liquid ammonia in an amount sufficient to act as both dehydrohalogenating agent and solvent, the said liquid ammonia containing an amount of an inorganic salt (hereinafter so designated) effective to accelerate the dehydrohalogenation reaction, wherein said inorganic salt is selected from the class consisting of ammonium chloride and bromide, lithium chloride and bromide, and sodium chloride and bromide, thereby to form a substantially pure dichloride of the above formula I, and removing the unreacted ammonia and inorganic salt, and isolating the desired dichloride.

U.S. Pat. No. 4,097,538—Factor et al, issued June 27, 1978 and assigned to the same assignee as the present invention, discloses the dehydrohalogenation of the compound of formula II with liquid ammonia wherein the latter is acting as both a dehydrohalogenating agent and as a solvent. As pointed out in that patent, this process produces the dichloride in high yield and of high purity. However, it has been found that the rate of dehydrohalogenation in the liquid ammonia is not as rapid as would be desired, and for optimum commercial utilization of this dehydrohalogenation process, it would be an important advantage to accelerate the rate of dehydrohalogenation.

In my U.S. patent application Ser. No. 4050 filed Jan. 17, 1979, and assigned to the same assignee as the present invention, is disclosed a process for dehydrohalogenating the above-identified trichloride to form the dichloride by using liquid methylamine as the dehydrohalogenating agent. As pointed out in this patent application, the liquid methylamine greatly accelerates the reaction whereby the dehydrochlorination takes place, although with sacrifice in the purity of the final dichloride.

It is accordingly one of the objects of the invention to effect dehydrohalogenation of the trichloride to the dichloride rapidly without sacrifice in the purity and yield of the dichloride.

It is a still further object of the invention to effect dehydrochlorination of the aforesaid trichloride using liquid ammonia as the dehydrohalogenating agent and yet be able to accelerate the dehydrohalogenating effect of the liquid ammonia, while at the same time maintaining the high purity and yield which accompany the use of the liquid ammonia alone.

Other objects of the invention will become more apparent from the discussion which follows.

In accordance with my invention, I have unexpectedly discovered that small amounts of inorganic salts of the class described above when added to liquid ammonia used as the dehydrohalogenating agent significantly increase the rate of dehydrohalogenation while retaining the advantages of the liquid ammonia in obtaining a high purity material in good yield. The dichloride thus obtained, after isolation needs little if any purification and can be used to make flame-resistant and flame-retardant resins by treatment of the dichloride of formula I with either diphenyl carbonate or phosgene to form polycarbonate resins.

It was entirely unexpected and in no way could have been predicted that the aforementioned class of inorganic salts would be able to accelerate the dehydrohalogenating action of the liquid ammonia. For example, under essentially equivalent conditions, it was found that an inorganic salt such as $NH_4F$ failed to reduce the rate of reaction and left an exceptionally large amount of the trichloride unreacted.

It was also surprising to find that the addition of these inorganic salts, particularly the $NH_4Cl$, would increase the rate of reaction without adversely affecting the reaction as far as the formation of the impurities are concerned. For instance, when liquid ammonia is used solely as the dehydrohalogenating agent (and as the solvent as well), $NH_4Cl$ is formed. It was surprising to find that even though $NH_4Cl$ was formed from the liquid ammonia originally used, the addition of preformed $NH_4Cl$ to the liquid ammonia greatly increased the rate of reaction of the liquid ammonia without adversely affecting the advantage of using liquid ammonia, namely, the low level of impurities.

The presence of the small amounts of the inorganic salt with the liquid ammonia does not interfere with the advantages inherent in the use of the ammonia itself. In the first place, no additional solvent of any kind is required since the ammonia acts as both the reactant and the solvent medium. In order to separate the dichloride from the reaction solution, one only needs to allow the ammonia to evaporate from the reactor and remove any inorganic salt by suitable means. Moreover, the dichloride obtained by this procedure after the by-product ammonium chloride and inorganic salt additives are removed (advantageously using a methanol-water medium or water washes) is free of usual impurities in products obtained by previous procedures at a similar stage of purification, for instance, by treating the trichloride with a large molar excess of aqueous sodium hydroxide at elevated temperatures [see M. Trojna and H. Hubacek, Chem. Listy 51, 752 (1957)]. If further purification of the dichloride by crystallization from methanol-water (whose pH has been adjusted to between 3 to 7) is used, the product obtained is as good if not better both in color and in freedom from impurities than products obtained by prior art procedures.

Although a large molar excess of ammonia is used to serve both as the reactant and the solvent medium, the dehydrochlorination only uses 1 mol of the ammonia per mol of trichloride, and at the end of the reaction the unused ammonia can be easily recovered by evaporation or distillation. Generally, on a molar ratio from 2 to 20 mols of ammonia are used per mol of the trichloride.

The amount of the inorganic salt used in combination with the liquid ammonia can be varied widely and only requires an amount of the former effective to induce the accelerated dehydrohalogenation action of the liquid ammonia. Based on the liquid ammonia employed, one can use from 0.5 to 20%, by weight, or more of the inorganic salt based on the weight of the ammonia. Stated alternatively, the inorganic salt can be used in amounts ranging from about 0.1 to 10 or more mol percent of the inorganic salt based on the molar concentration of the liquid ammonia.

In accordance with my invention, the dehydrochlorination of the trichloride can be achieved by charging the trichloride to a pressure reactor together with the liquid ammonia and the inorganic salt, and thereafter heating the pressure reactor at temperatures ranging from 35° to 125° C. and preferably from 50° to 100° C., for times ranging from about 30 minutes to 6 hours or more to effect dehydrohalogenation. Thereafter, the formed dichloride can be removed from the liquid ammonia-inorganic salt mixture and the ammonium chloride formed, by first allowing the ammonia to volatilize and collecting the latter, and then dissolving the remaining solid material in aqueous methanol and crystallizing the dichloride from that solution by adding water in which the dichloride is insoluble. If further purification is desired, the dichloride can be recrystallized in the manner described above with a methanol-water mixture. It is evident that the size of the pressure reactor used will in many instances dictate the molar concentrations of the ammonia, the inorganic salt, and the trichloride undergoing dehydrohalogenation.

Depending on the temperatures and the amount of ammonia and inorganic salt present in the reactor, pressures ranging from 50 psi to 700–800 psi or more can be employed without materially affecting the results. Again, the temperatures used will depend on the type and size of the pressure reactor employed, the molar concentrations of the ammonia, inorganic salt, the trichloride, etc. Because the reaction using the inorganic salt with the ammonia can be run at somewhat lower temperatures than when ammonia is used alone without any significant increase in impurities, total reaction times of shorter duration are possible than with other methods for dehydrohalogenation. Thus, it has been found that at any reasonable temperature of reaction (50° to 100° C.) the combination of the ammonia and the inorganic salt will cause completion of the dehydrohalogenation reaction in a significantly shorter time than when the ammonia is used alone.

Under the pressure conditions employed in the practice of my invention, temperature, of course is an important function in the attainment of a substantially pure dichloride. Thus, as one proceeds from around room temperature (about 20°–30° C.) to about 125° C., one will find that with the use of reasonable times of reaction, for instance, about 30–90 minutes at the upper end of the temperature range, essentially all of the trichloride is converted to the dichloride in a substantially pure state.

Although the reaction between the ammonia and the trichloride can be carried out without any additional ingredients, the use of aprotic solvents is not precluded. Included among such solvents may be mentioned dimethyl formamide, N-methyl pyrrolidone, N,N-dimethylacetamide, dimethyl sulfoxide, etc. Amounts of such solvents, for instance, by weight, from about 0.1 to 2 parts of the solvent per part of the trichloride, can be used to advantage in some instances in order to reduce the amount of excess liquid ammonia which may be required.

In order that those skilled in the art may better understand how the present invention may be practiced, the following examples are given by way of illustration and not by way of limitation. In some instances, the amounts of ingredients used in the reaction are recited both on a weight and mol percent basis.

In some of the work which will be described below, measurements were made to determine the amount of impurities, particularly those having the formulas

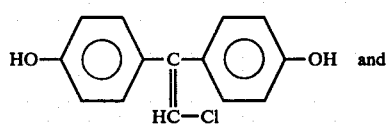

III

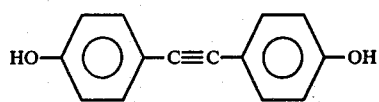

IV which are present after the dehydrohalogenation reaction has been carried out and the desired dichloride isolated. The amount of these two impurities determines how pure a dichloride was obtained by the claimed reaction. For determining the amount of impurities, a Waters Model 244 liquid chromatograph was used equipped with a Model U6K injector, a $\mu C_{18}$ Bondapak column, a Model 440 detector equipped with a 10 mm cell and operated at 280 nm set at 0.1 AUFS and a 10 millivolt Houston Instrument Omniscribe recorder with a chart speed of 0.25 centimeter per minute. Ten microliters of a 10% (wt./vol.) methanol solution of the dichloride is injected into the column and it is eluted at 2 ml per minute, where the solvent mixture is programmed linearly over a 1 hour period from an initial composition of 40% methanol and 60% water to a final composition of 100% methanol.

EXAMPLE 1

About 20 ml (13 grams, 0.765 mol) ammonia was condensed at −78° C. in a pressure reactor containing 0.6 gram (0.00189 mol) of the trichloride and a stated amount of the specified inorganic halide. After the ammonia had been condensed, the pressure reactor was sealed and warmed to 50° C., at which point the pressure rose to about 220 psi. The reaction was then allowed to proceed with stirring for a period of about 18 hours. The reaction mixture was then quenched by cooling the reaction vessel to −78° C., the reaction vessel opened, and the ammonia allowed to evaporate. The residue was dissolved in 9 ml 80% aqueous methanol, and acidified with concentrated HCl (about 2 ml) to a pH of 4. The solution was filtered and the reactor washed with an additional 3 ml of methanol which was added to the filtrate. The filtrate now contained the desired dichloride of formula I and all the ammonium chloride or other inorganic halide used. The filtrate was further diluted with 12 ml water and upon heating to 75°–80° C., the solution became homogeneous. This homogeneous solution was then cooled and the product of white crystals which separated out was collected by filtration. In the case where 2.52 mol percent NH$_4$Cl was used, the first crop of crystals in this test yielded 0.456 gram (85.8% yield) of the dichloride of formula I; this crystalline product, when analyzed by high pressure liquid chromatography described previously, showed that there were less than 50 parts per million of the trichloride, 30 parts per million of the monochloride impurity having formula III, and no detectable amount of the acetylene compound impurity of formula IV, both of these compounds being the more troublesome impurities in the dehydrohalogenation product derived from the trichloride. The second crop of crystals from the mother liquid afforded an additional 0.063 gram of dichloride, giving a total isolated yield of 97.7% for the trichloride. It is thus evident from the high pressure liquid chromatographic analysis that the addition of ammonium chloride to the ammonia in the dehydrohalogenation reaction did not cause any increase in impurities as compared to when the liquid ammonia was used alone as the dehydrohalogenating agent. The following Table I shows the results of tests employing other inorganic salts using the same conditions conducted with the above-described ammonium chloride. The ammonium fluoride test was carried out to show that unexpectedly all inorganic salts did not work. The heading in the table "$T_{1/2}$ (minutes)" is indicative of the half-life of the reaction and of the rate of the dehydrohalogenation; the smaller the figure for the $T_{1/2}$, the faster the rate of reaction. It should also be noted that the ammonium bromide, which was almost as fast as the ammonium chloride when added to the liquid ammonia, also produced dichloride which had the same low level of impurities as when the ammonium chloride was used.

[1]TABLE I

| Inorganic Salt | [2]Weight Percent | [2]Mol Percent | [3]Percent Trichloride | $T_{\frac{1}{2}}$(minutes) |
|---|---|---|---|---|
| NH$_4$Cl | 7.92 | 2.52 | 20.7 | 26 |
| NH$_4$Cl | 11.01 | 3.50 | 19.4 | 25 |
| NH$_4$Br | 14.23 | 2.47 | 26.4 | 31 |
| LiCl | 6.15 | 2.47 | 30.5 | 35 |
| NaCl | 8.46 | 2.47 | 32.1 | 38 |
| NH$_4$F | 5.38 | 2.47 | 44.7 | 52 |
| MgCl$_2$ | 13.85 | 2.47 | 46.6 | 55 |
| None | — | — | 45.6 | 53 |

[1]Amounts of reactants same except for inorganic salt.
[2]Based on NH$_3$.
[3]Mol percent after 60 minutes at 50° C.

EXAMPLE 2

When the bromides of lithium and sodium are substituted for the corresponding chlorides of Example 1, under the same conditions of reaction, it will be found that the half-life of dehydrohalogenating the trichloride with ammonia will also be significantly reduced as compared to the half-life obtained using liquid ammonia free of any such bromides in the dehydrohalogenation reaction.

The use of small amounts of the inorganic halides in combination with the liquid ammonia will allow the use of lower temperatures and lower pressures and still achieve rapid reaction times. Thus, since the rate at 50° C. is more than doubled by the addition of at low as 1.5 mol percent NH$_4$Cl to ammonia (10:1 mol ratio NH$_4$Cl to trichloride), one could decrease the temperature by at least 10° and have the same reaction rate as obtained with pure ammonia at 50° C. The requirements of very high pressure equipment to contain the ammonia can now be decreased because lower temperatures can be used to achieve the same rates.

The dichloride obtained in accordance with the present invention has many uses. One of the more important uses to which this composition may be put is as an intermediate in the preparation of heat-resistant polyester resins. For instance, the dichloride can be reacted with phthalic acid esters or certain phthalic acids themselves, such as dimethyl terephthalate, terephthalic acid, isophthalic acid, etc., to make polyester resins. An important use for the dichloride is in the preparation of flame and heat resistant polycarbonate resins by reacting the dichloride with precursor carbonating agents, such as phosgene, diphenyl carbonate, etc.

The polymeric compositions derived from the reaction of the dichloride here described have many applications. These polymeric compositions may be used to form fibers, films, or molded products. Thus, either by extrusion from melt or by depositing from solution, fibers derived from these polymeric compositions may be formed and used in the preparation of various textile materials designed for clothing and similar applications.

Various fillers may be incorporated in the polymeric compositions prior to molding thereof. Among such fillers may be mentioned glass fibers, carbon black, titanium dioxide, silica, mica, bentonite, etc. Molded products derived from such a mixture of ingredients can be used as gears, handles for cooking utensils, etc. The incorporation of abrasive particles such as carborundum, diamond powder, etc., makes molded products derived from such polymeric compositions useful as grinding wheels, etc. The addition of carbon, silicon carbide, powdered metal, conducting oxides, etc., to the polymeric compositions results in the so-called resistance or semiconducting paints which have many useful applications.

It will of course be understood by those skilled in the art that in addition to the conditions, ingredients, and concentrations of ingredients described in the foregoing examples, other conditions, ingredients, and concentrations, examples of which are discussed previously, may be used without departing from the scope of the invention. It is intended to include within the scope of the claims herein appended any changes or modifications which may be indicated as advantageous in the practice of the invention.

What I claim as new and desire to secure by Letters Patent of the United States is:

1. In the process for dehydrohalogenating the trichloride, 1,1,1-trichloro-2,2-bis(4-hydroxyphenyl) ethane, to form the dichloride of the formula

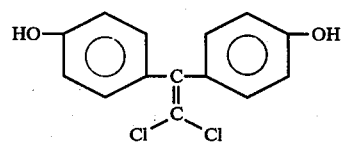

by treating the aforesaid trichloride with anhydrous liquid ammonia in an amount sufficient to act as both a dehydrohalogenating agent and solvent, the improvement which comprises adding to the liquid ammonia an amount of an inorganic halide effective to accelerate the dehydrohalogenation reaction of the ammonia, wherein said inorganic halide is selected from the class consisting of ammonium chloride and bromide, lithium chloride and bromide, and sodium chloride and bromide.

2. The process as in claim 1 wherein the inorganic halide comprises from 0.5 to 20%, by weight, based on the weight of the ammonia.

3. The process as in claim 1 wherein there is present a molar ratio of from 2 to 20 mols liquid ammonia per mol trichloride.

4. The process as in claim 1 wherein the inorganic halide is $NH_4Cl$.

5. The process as in claim 1 wherein the inorganic halide is lithium chloride.

6. The process as in claim 1 wherein the inorganic halide is sodium chloride.

7. The process as in claim 1 wherein the inorganic halide is $NH_4Br$.

8. In the process for dehydrohalogenating the trichloride, 1,1,1-trichloro-2,2-bis(4-hydroxyphenyl) ethane, to form the dichloride of the formula

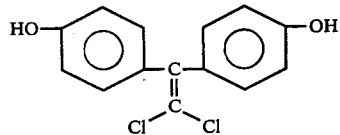

whereby the aforesaid trichloroethane is treated with anhydrous liquid ammonia in an amount sufficient to act as both dehydrohalogenating agent and solvent, the improvement whereby an amount of $NH_4Cl$ is added to the liquid ammonia effective to accelerate the dehydrohalogenation reaction of the ammonia.

* * * * *